United States Patent [19]

Vletter

[11] Patent Number: Plant 7,091

[45] Date of Patent: Jan. 2, 1990

[54] LILY PLANT NAMED MONTE ROSA

[75] Inventor: Floris Vletter, Rijnsburg, Netherlands

[73] Assignee: Gebr. Vletter & J.A. den Haan, Netherlands

[21] Appl. No.: 261,252

[22] Filed: Oct. 24, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new lily plant named Monte Rosa characterized by its attractive pink flower coloring.

2 Drawing Sheets

The present invention comprises a new and distinct cultivar of lily, botanically known as Lilium (Asiatic hybrid), and hereinafter referred to by the cultivar name Monte Rosa.

Monte Rosa is a product of a planned breeding program which had the primary objective of creating new lily cultivars with pink coloring.

Monte Rosa was originated by me from a hybridization made in a controlled breeding program in Rijnsburg, The Netherlands. The female parent was an unnamed, unpatented seedling designated F2.76-33 and the male parent was an unnamed, unpatented seedling designated RS.403.

Monte Rosa was discovered and selected by me as one flowering plant within the progeny of the stated cross in a controlled environment in Rijnsburg, The Netherlands.

I accomplished the first act of asexual reproduction of Monte Rosa by scaling bulbs of the initial selection in August 1980 in a controlled environment in Rijnsburg. Horticultural examination of selected units initiated in October 1983 has demonstrated that the combination of characteristics as herein disclosed for Monte Rosa are firmly fixed and are retained through successive generations of asexual reproduction.

In describing the characteristics of the variety, the guidelines for the species Lilium promulgated by the International Union for the Protection of New Varieties of Plants (UPOV) have been applied. These descriptors appear in parentheses in the detailed description of the characteristics of the variety. The specific dimensions of the various parts of the plant depend on the circumstances of growing (for example, light intensity).

Monte Rosa has not been observed under all possible environmental conditions. The phenotype may vary significantly with variations in environment such as temperature, light intensity, and day length. The following observations, measurements, and comparisons describe plants grown in Wageningen, The Netherlands under greenhouse conditions which approximate those generally used in commercial practice.

The following traits have been repeatedly observed and are determined to be basic characteristics of Monte Rosa which in combination distinguish this lily as a new and distinct cultivar.

1. Flowers of Monte Rosa have distinctive pink coloring.

2. Flower color turns to near RHS 55B to 55C tinged with blue, but with less orange at center, near RHS 24C to 24D.

3. Branches make an angle of about 45°-60° with peduncle.

4. Petals overlap in closed flower.

5. Narrow honey gland, thick with transparent white gland hairs, around which are several stalked papillas, with gland hairs, on top.

The accompanying photographic drawings show the flower characteristics of Monte Rosa, with colors being as true as possible with illustrations of this type. Photographic Sheet 1 is a perspective view of a branch of the variety in full blossom. Photographic Sheet 2 is a closeup of a mature blossom of the variety, indicating its coloration and configuration.

In the following description, color references are made to The Royal Horticultural Society Colour Chart (RHS).

Origin: Seedling.

Parentage:

*Seed parent.*—Unknown seedling.

*Pollen parent.*—Unknown seedling.

*Classification.*—Asiatic hybrid.

Plant:

1. *Plant height (on opening of the anthers of the first flower).*—Medium (5).
2. *Stalk.*—Anthocyanin coloring — weak at the base. Color: light green (1). Growth of hair: present (9). Type of coat of hair: long (2). Division of coat of hair: mainly in leaf axils, distal (1). Internode length: uniform (2). Cross section: ribbed (3). Bulbils: lacking (1).
3. *Leaf.*—Position: spread out (2). Top angle of the base with the stalk: sharp, about 45° (4). Length: medium (5). Width: medium (5).

Flower:

1. *Structure (number of bracteoles in comparison with the total number of flowers).*—Equal (1). Position: erect to horizontal (3). Type: bowl-shaped, weak (3). Cross-section: medium (5). Height of crown: medium (5). Length of longest flower stalk: medium (5).
2. *Petals.*—Length of longest exterior petal: medium (5). Width of widest exterior petal: medium (5). Length of longest interior petal: medium (5). Width of widest interior petal: wide (7). Color of the inside of the interior petal: near 48B, to near 54C, but more diffuse; center near 24B; distal lighter, near 54C, but a little bluer in center with large diffuse orange spot, near 24B. Color of the outside of the interior petal: near 54D at wings, with the exception of the top which is darker near 51B to 181C, but more diffuse. Color of the inside of the exterior petal: near 54C, somewhat darker along edges; middle nerve greenish; top slightly thickened and green. Color of the outside of the exterior petal: variable, with some fine dark brown spots. Color of the inside of the throat: near 55C. Color of the outside of the throat: near 55C to 55D. Surface structure of the inside: ribbed and papillate, honey gland about 20 mm long. (4). Luster at the inside: lacking. (1). Curve of the edges of the petal: lacking. (1). Flexure of petals: present. (9). Bended part of the petals: only top. (1). Extent of bending: weak to medium, exterior petals medium, interior petals weak. (4). Fragrance: lacking. (1).

Reproductive organs:

*Length of stamina.*—Medium. (5).

*Color of the filaments.*—White, on top with hint of pink. (1).

*Color of the anthers.*—Orange (unripe); sometimes lacking.

*Color of pollen.*—Orange.

*Length of the pistil.*—Medium. (5).

*Color of the style.*—Green, with weak hint of red. (2).

*Color of the stigma.*—Green, very poorly occupied by reddish purple gland hairs. (1).

Bulb:

*Type (in period of rest).*—type 2.

*Top.*—Pointed. (1).

*Density of scales.*—Close. (1).

*Color of the exterior scales.*—White with purple.

*Top of the scales.*—Pointed. (1).

*Underground part of the stalk.*—Bulbils — present. (9) roots — present. (9).

I claim:

1. A new and distinct variety of lily plant named Monte Rosa, substantially as shown and described.

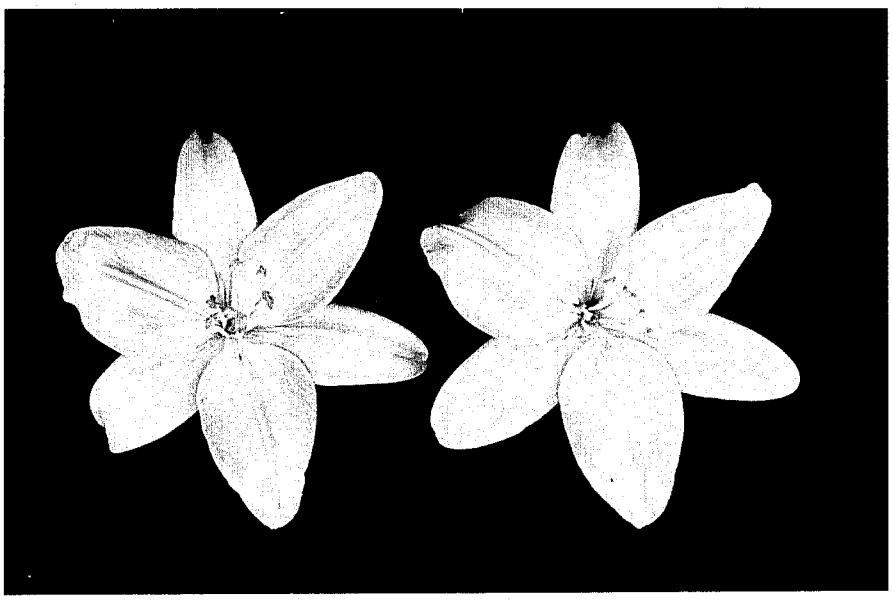

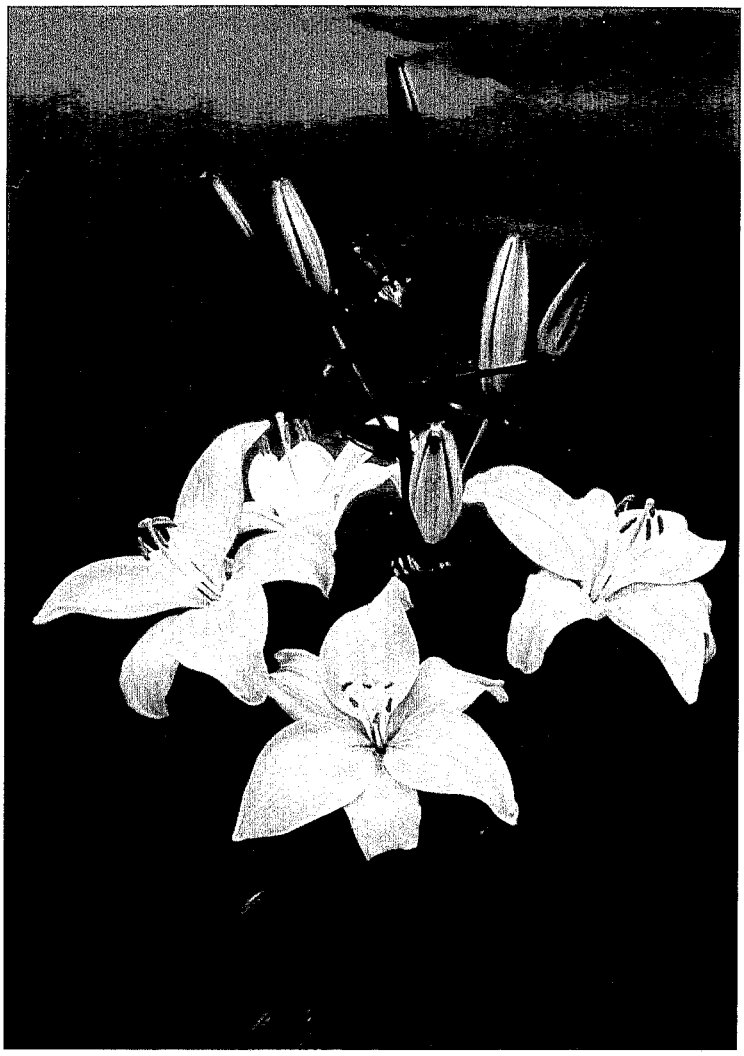

* * * * *